(12) United States Patent
Feng et al.

(10) Patent No.: US 11,980,454 B2
(45) Date of Patent: May 14, 2024

(54) MICROCIRCULATORY HIGH-VELOCITY BLOOD FLOW THRESHOLD INDEX AND MEASUREMENT AND CALCULATION SYSTEM AND METHOD THEREOF

(71) Applicant: XUZHOU LIHUA ELECTRONIC TECHNOLOGY DEVELOPMENT CO., LIMITED, Xuzhou (CN)

(72) Inventors: Xinghuai Feng, Xuzhou (CN); Hui Feng, Xuzhou (CN); Jie Shao, Xuzhou (CN); Jing Lu, Xuzhou (CN); Yuanchang Zhang, Xuzhou (CN)

(73) Assignee: XUZHOU LIHUA ELECTRONIC TECHNOLOGY DEVELOPMENT CO., LIMITED, Xuzhou (CN)

( * ) Notice: Subject to any disclaimer, the term of this patent is extended or adjusted under 35 U.S.C. 154(b) by 478 days.

(21) Appl. No.: 17/405,053

(22) Filed: Aug. 18, 2021

(65) Prior Publication Data
US 2022/0061682 A1 Mar. 3, 2022

(30) Foreign Application Priority Data
Sep. 1, 2020 (CN) .......................... 202010905859.2

(51) Int. Cl.
*A61B 5/026* (2006.01)
*A61B 5/00* (2006.01)
*G06T 7/00* (2017.01)

(52) U.S. Cl.
CPC .......... *A61B 5/0261* (2013.01); *A61B 5/0077* (2013.01); *A61B 5/412* (2013.01); *G06T 7/0012* (2013.01); *G06T 2207/30104* (2013.01)

(58) Field of Classification Search
CPC .............. A61B 5/0077; A61B 5/02007; A61B 5/02028; A61B 5/0261; A61B 5/412; G06T 2207/30104; G06T 7/0012; Y02A 90/10
See application file for complete search history.

(56) References Cited

U.S. PATENT DOCUMENTS

| 5,579,774 A | * | 12/1996 | Miller ................... A61B 5/031 600/487 |
| 2006/0142746 A1 | * | 6/2006 | Friedman ............. A61B 18/203 606/11 |

(Continued)

FOREIGN PATENT DOCUMENTS

WO    2017121279 A1    7/2017

OTHER PUBLICATIONS

Daniel S. Martin, "Abnormal blood flow in the sublingual microcirculation at high altitude," Mar. 31, 2009, Eur J Appl Physiol (2009) 106, pp. 473-476.*

(Continued)

*Primary Examiner* — Omar S Ismail
(74) *Attorney, Agent, or Firm* — Bayramoglu Law Offices LLC

(57) ABSTRACT

A system for measurements and calculations of a microcirculatory high-velocity blood flow includes a data acquisition module configured to select and acquire microcirculatory blood vessel image data; a storage module configured to store the acquired microcirculatory blood vessel image data; a velocity measurement module configured to measure a traveling distance and a traveling time of red blood cell (RBC), white blood cell (WBC), or plasma particles in a blood vessel sample and calculate a ratio of the traveling distance to the traveling time to obtain a blood flow velocity; and a high-velocity blood flow index module configured to determine an index level for the microcirculatory high- (Continued)

velocity blood flow. Specifically, an initial threshold, i.e. 1000 μm/s, for the microcirculatory high-velocity blood flow of sepsis is proposed, which facilitates early diagnosis on sepsis. The changing process of the high-velocity blood flow shows development of the early-stage, intermediate-stage and end-stage sepsis.

8 Claims, 1 Drawing Sheet

(56) References Cited

U.S. PATENT DOCUMENTS

| | | | |
|---|---|---|---|
| 2010/0027857 A1* | 2/2010 | Wang | A61B 5/0066 382/128 |
| 2010/0104168 A1* | 4/2010 | Dobbe | A61B 5/02007 382/128 |
| 2011/0189166 A1* | 8/2011 | Boucher | A61K 38/44 424/94.4 |
| 2011/0289043 A1* | 11/2011 | Suresh | B01L 3/502746 703/2 |
| 2012/0053918 A1* | 3/2012 | Taylor | G16H 50/50 703/9 |
| 2013/0107274 A1* | 5/2013 | Vertikov | G01B 9/02027 356/479 |
| 2015/0038860 A1* | 2/2015 | Fonte | A61B 6/507 600/505 |
| 2015/0141804 A1* | 5/2015 | Rooney | A61B 5/0263 600/419 |
| 2015/0209449 A1* | 7/2015 | Pan | A61B 5/0275 424/9.1 |
| 2016/0070877 A1* | 3/2016 | Taylor | A61B 5/029 703/9 |
| 2018/0055572 A1* | 3/2018 | Spilker | G16H 50/20 |
| 2018/0064731 A1* | 3/2018 | Macdonald | A61K 31/4422 |
| 2021/0251599 A1* | 8/2021 | Torp | A61B 8/488 |

OTHER PUBLICATIONS

Francesca Sapuppo,"An Improved Instrument for Real-Time Measurement of Blood Flow Velocity in Microvessels," May 17, 2007, IEEE Transactions on Instrumentation and Measurement, vol. 56, No. 6, Dec. 2007, pp. 2663-2669.*

Paul WG Elbers, "Bench-to-bedside review: Mechanisms of critical illness-classifying microcirculatory flow abnormalities in distributive shock," Jul. 19, 2006,Critical Care 2006, 10:221 (doi:10.1186/cc4969), pp. 1-6.*

Jim O'Doherty,"Comparison of instruments for investigation of microcirculatory blood flow and red blood cell concentration," Jun. 17, 2009, Journal of Biomedical Optics 14(3), 034025(May/Jun. 2009),pp. 034025-1-034025-10.*

Daniel De Backer,"How to evaluate the microcirculation: report of a round table conference," Sep. 10, 2007,Critical Care 2007, 11:R101 (doi:10.1186/cc6118),pp. 1-6.*

Fei Ye,"In-vivo full-field measurement of microcirculatory blood flow velocity based on intelligent object identification," Jan. 22, 2020, Journal of Biomedical Optics,vol. 25(1) , pp. 016003-1-016003-8.*

Sam Eriksson et al., "Non-invasive imaging of microcirculation: a technology review," Dec. 21, 2022,Medical Devices: Evidence and Research,DOI: 10.2147/MDER.S51426,pp. 445-449.*

Chao Liu,"Real-time Visual Analysis of Microvascular Blood Flow for Critical Care," Jun. 2015,Proceedings of the IEEE Conference on Computer Vision and Pattern Recognition (CVPR), 2015, pp. 2217-2223.*

Matthias Jacob, "Regulation of blood flow and volume exchange across the microcirculation," Oct. 21, 2016,Critical Care (2016) 20:319,pp. 1-10.*

Can Ince et al.,"Second consensus on the assessment of sublingual microcirculation in critically ill patients: results from a task force of the European Society of Intensive Care Medicine," Feb. 6, 2018, Intensive Care Med (2018) 44:, pp. 282-295.*

Vanina S. Kanoore Edul,"Similar Microcirculatory Alterations in Patients with Normodynamic and Hyperdynamic Septic Shock," Nov. 10, 2015, Ann Am Thorac Soc vol. 13, No. 2,pp. 240-245.*

Boris Chayer,"Velocity measurement accuracy in optical microhemodynamics: experiment and simulation," Sep. 4, 2012, Physiol. Meas. 33 (2012), pp. 1587-1595.*

Yasuhiko Sugii,"Velocity measurement of both red blood cells and plasma of in vitro blood flow using high-speed micro PIV technique," Jan. 7, 2005,Meas. Sci. Technol. 16 (2005),pp. 1126-1128.*

Dawei Liu, et al., Clinical Hemodynamics, 2013, pp. 64-65, 299-300, 220-300, First Edition, People's Medical Publishing House.

Paul WG Elbers, et al., Bench-to-bedside review: Mechanisms of critical illness-classifying microcirculatory flow abnormalities in distributive shock, Critical Care, 2006, pp. 1-8, 10:221.

Daniel De Backer, et al. How to evaluate the microcirculation: report of a round table Conference, Critical Care, 2007, pp. 1-9, vol. 11 No. 5.

Vanina S. Kanoore Edul, et al., Similar Microcirculatory Alterations in Patients with Normodynamic and Hyperdynamic Septic Shock, ANNALSATS, 2015, pp. 1-23.

Vanina S. Kanoore Edul, et al., Quantitative assessment of the microcirculation in healthy volunteers and in patients with septic shock, Crit. Care Med., 2012, pp. 1443-1448, vol. 40, No. 5.

Vanina S. Kanoore Edul, et al., What is microcirculatory shock?, Curr Opin Crit Care, 2015, pp. 245-252, vol. 21 No. 3.

Can Ince, et al., Second consensus on the assessment of sublingual microcirculation in critically ill patients: results from a task force of the European Society of Intensive Care Medicine, Intensive Care Med., 2018, pp. 281-299, 44.

Danian Zhu, et al., Physiology, 2004, pp. 125, People's Medical Publishing House.

Youning Liu, et al., Compilation of papers on lung infection, respiratory failure and SARS nationwide, Chinese Medical Journal, 2004, pp. 371-375.

Christopher W Seymour. et al, Assessment of Clinical Criteria for Sepsis for the Third International Consensus Definitions for Sepsis and Septic Shock (Sepsis-3), JAMA, 2016, pp. 762-774, vol. 315 No. 8.

* cited by examiner

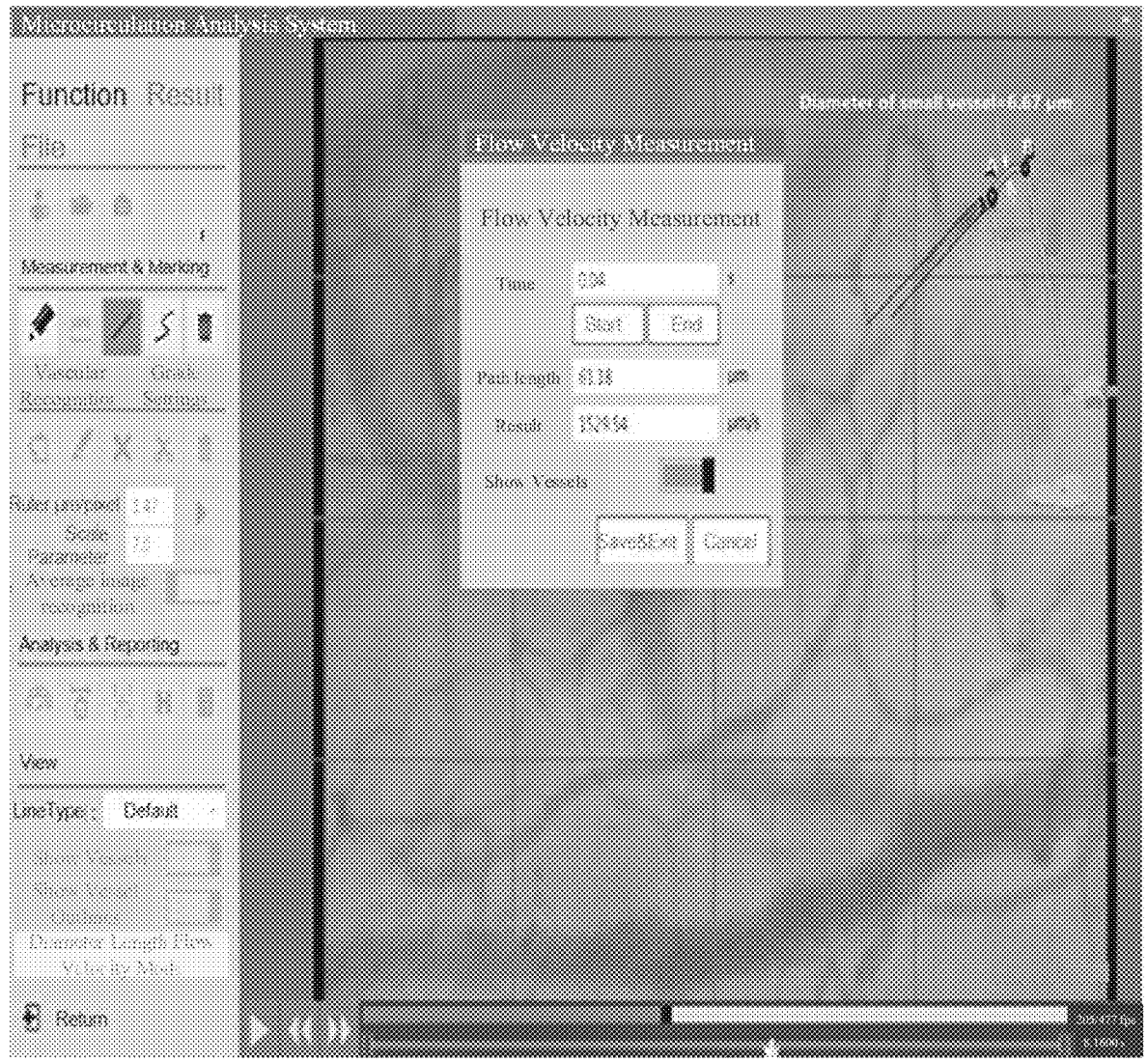

MICROCIRCULATORY HIGH-VELOCITY BLOOD FLOW THRESHOLD INDEX AND MEASUREMENT AND CALCULATION SYSTEM AND METHOD THEREOF

CROSS REFERENCE TO THE RELATED APPLICATIONS

This application is based upon and claims priority to Chinese Patent Application No. 202010905859.2, filed on Sep. 1, 2020, the entire contents of which are incorporated herein by reference.

TECHNICAL FIELD

The present disclosure belongs to the technical field of medical monitoring, and in particular relates to a system for measurements and calculations of microcirculatory blood flows.

BACKGROUND

At present, in European and American medical communities of critical care, high-velocity blood flow in the microcirculation is called a hyperdynamic microvascular blood flow. In the early papers on the observation of sublingual microcirculation prior to 2006, the European and American medical communities of critical care once regarded the hyperdynamic microvascular blood flow as the fifth pattern of microcirculation, as elaborated in Literature [2]. However, as of 2018, the mainstream opinions in related research in the west had expressed incomprehension on this phenomenon or even directly denied its existence, as elaborated in Literatures [3] [4] [5], and [6].

Over the three years after the publication of the PCT patent application (PCT/CN2017/070249, WO/2017/121279) of the inventors on the website of the World Intellectual Property Organization (WIPO) on Jul. 20, 2017, some studies begun to conditionally recognize the existence of hyperdynamic microvascular blood flow, as elaborated in literature [7]. However, this recognition is still very limited. For example, in the "Second Consensus on the Assessment of Sublingual Microcirculation in Critically Ill Patients" (hereafter referred to as "consensus") formulated at the international expert meetings held by the European Society of Intensive Care Medicine (ESICM) in 2018, the previously denied hyperdynamic microvascular blood flow was regarded as the fourth type: hyperdynamic circulation in capillaries. The qualitative classification in 2006 was rewritten into the consensus once again, but the high-velocity blood flow (hyperdynamic microvascular blood flow) was not quantitatively defined in the form of accurate numerical values (as defined for a threshold of high-velocity blood flow below) and thus no substantial progress was made, which shows that there is still a lack of essential understandings and recognitions for the high-velocity blood flow.

In addition, the space-time diagram (STD) (namely, the space-time method) is commonly recognized as an algorithm for measuring the high-velocity blood flow internationally. According to the second international consensus of the European Society of Intensive Care Medicine (ESICM) in 2018 (literature 7), the European and American academic consensus in the art insisted that: the STD is a gold standard for the quantitative measurement of red blood cell (RBC) flow velocity. However, the research and practice of the present disclosure show that a computer can automatically identify the trajectory, shape, and gray level of moving RBC particles, white blood cell (WBC) particles, and plasma particles in the microcirculation with a low blood flow velocity of about 500 μm/s (because in this case, the trajectory, shape, and gray level of the moving RBC particles, WBC particles, and plasma particles do not change significantly). However, in case of a high-velocity blood flow, the trajectory, shape, and gray level of moving RBC particles, WBC particles, and plasma particles change so significantly that the trajectory of the moving RBC particles, WBC particles, and plasma particles cannot be accurately tracked by the space-time method in most cases, as a result, it is unable to create a projection on a two-dimensional plane, and thus the length of an adjacent side cannot be calculated by a trigonometric function. Therefore, the space-time method is difficult to successfully measure the velocity of a high-velocity blood flow, and thus cannot be widely used in the measurement of a microcirculatory blood flow velocity of higher than 1,000 μm/s.

Literature [1]: Liu Dawei, Qiu Haibo, Yan Jing, et al., Clinical Hemodynamics. [M] People's Medical Publishing House, First Edition, Beijing 2013: 64-65, 299-300, 220-221.

Literature [2]: Paul W G Elbers and Can Ince et al., Bench-to-bedside review: Mechanisms of critical illness classifying microcirculatory flow abnormalities in distributive shock [J], Critical Care 2006, 10:221 (doi: 10.1186/cc4969)

Literature [3]: Daniel De Backer, Steven Hollenberg, Christiaan Boerma, et al., How to evaluate the microcirculation: report of a round table Conference [J]. Critical Care 2007, 11: R101 (doi:10.1186/cc6118)

Literature [4]: Vanina S. Kanoore Edul, Can Ince, Alejandro Risso Vazquez. et al., Similar Microcirculatory Alterations in Patients with Normodynamic and Hyperdynamic Septic Shock [J]. ANNALSATS Articles in Press. Published on 1 Dec. 2015 as 10.1513/AnnalsATS.201509-606OC. the American Thoracic Society.

Literature [5]: Vanina S. Kanoore Edul, M D et al.; Quantitative assessment of the microcirculation in healthy volunteers and in patients with septic shock [J] Crit Care Med 2012 Vol. 40, No. 5

Literature [6]: Vanina S. Kanoore Edula, b, Can Ince et al, What is microcirculatory shock [J] Curr Opin Crit Care 2015, 21: 245-252

Literature [7]: Can Ince, E. Christiaan Boerma, et al, Second consensus on the assessment of sublingual microcirculation in critically ill patients: results from a task force of the European Society of Intensive Care Medicine Literature [8]: Zhu Danian, et al., Physiology, 9th edition [M], page 125, Beijing, People's Medical Publishing House, September 2018.

SUMMARY

In order to overcome the above-mentioned limitations of the prior art, the present disclosure provides indexes for a microcirculatory high-velocity blood flow, and a system and method for measurements and calculations of a microcirculatory high-velocity blood flow, which can accurately measure a high-velocity blood flow velocity of higher than 1,000 μm/s. The present invention solves the problem that there is no index for the microcirculatory high-velocity blood flow in the prior art, and the problem that the current mainstream measurement method cannot measure and calculate the microcirculatory high-velocity blood flow.

The present disclosure is implemented by the following technical solutions:

A system for measurements and calculations of a microcirculatory high-velocity blood flow is provided, including:

a data acquisition module configured to select and acquire microcirculatory blood vessel image data;

a storage module configured to store the acquired microcirculatory blood vessel image data;

a velocity measurement module configured to measure a traveling distance and a traveling time of RBC, WBC, or plasma particles in a blood vessel sample and calculate a ratio of the traveling distance to the traveling time to obtain a blood flow velocity; and a high-velocity blood flow index module configured to determine an index level for the microcirculatory high-velocity blood flow, where the microcirculatory high-velocity blood flow is defined as a microcirculation manifestation of a macro-hemodynamic high output-low resistance phenomenon in a resting state; and specifically, a blood flow velocity of higher than 1,000 μm/s in an arteriole, a venule, and a true capillary exchange network of a microcirculatory capillary circuitous channel is set as an initial threshold for the high-velocity blood flow.

The high-velocity blood flow index module may include the following three parameter indexes:

a first level: a blood flow velocity of higher than or equal to 1,000 μm/s and less than 1,300 μm/s in a microcirculatory network capillary, indicating that it is suspected of high-velocity blood flow;

a second level: a blood flow velocity of higher than or equal to 1,300 μm/s and less than 1,500 μm/s in a microcirculatory network capillary, indicating that it is highly suspected of high-velocity blood flow; and a third level: a blood flow velocity of higher than or equal to 1,500 μm/s in a microcirculatory network capillary, indicating that there is definitely a microcirculatory high-velocity blood flow.

The system for measurements and calculations of a microcirculatory high-velocity blood flow may further include a high-velocity blood flow template or rapid identification image index module; the high-velocity blood flow template or rapid identification image index module may store a blood vessel image with a blood flow velocity of higher than 1,000 μm/s as a high-velocity blood flow template or a rapid identification image index; and the rapid identification image index may include: "waterfall blood flow", which refers to a blood flow phenomenon that a blood flow velocity in a large capillary network with a diameter of greater than or equal to 20 μm is higher than or equal to 1,500 μm/s; and "flying mosquitoes blood flow", which refers to a blood flow phenomenon that a blood flow velocity in a capillary network with a diameter of less than 20 μm is higher than or equal to 1,500 μm/s.

A method for measurements and calculations of a microcirculatory high-velocity blood flow is provided, including the following steps:

step 1: defining the microcirculatory high-velocity blood flow as a microcirculation manifestation of a macro-hemodynamic high output-low resistance phenomenon in a resting state, and specifically, setting a blood flow velocity of higher than 1,000 μm/s in an arteriole, a venule, and a true capillary exchange network of a microcirculatory capillary circuitous channel as an initial threshold for the high-velocity blood flow;

step 2: using a microcirculation observation device to select 3 to 5 observation regions at sublingual mucosa or other parts of a body that allow microcirculation observation and record videos of the observation regions; comparing the videos of the 3 to 5 observation regions, selecting a video with the highest blood flow velocity as a high-velocity blood flow candidate sample A1 from videos each with a blood vessel having a blood flow velocity of higher than 1,000 μm/s, and storing the high-velocity blood flow candidate sample A1 in a sample database; and selecting a blood vessel B1 with the highest blood flow velocity in the candidate sample A1 as a high-velocity blood flow candidate blood vessel sample A1-B1, regardless of the diameter of the blood vessel, which is the most fundamental principle of the method; and step 3: tracking a trajectory of RBC, WBC, or plasma particles in the high-velocity blood flow on a display screen, calculating a traveling distance and a corresponding traveling time of the tracked RBC, WBC, or plasma particles with the aid of a computer, and dividing the traveling distance by the traveling time to calculate an average blood flow velocity of the high-velocity blood flow, which solves the problem that the current mainstream measurement method is difficult to accurately measure a high-velocity blood flow velocity of higher than 1,000 μm/s.

The method for measurements and calculations of a microcirculatory high-velocity blood flow may further include step 4: evaluating the microcirculatory high-velocity blood flow; and because a current technical means fails to measure a velocity of a high-velocity blood flow very accurately, a measured blood flow velocity of higher than or equal to 1,000 μm/s and less than 1,300 μm/s in a microcirculatory network capillary is used as a suspected high-velocity blood flow index, a measured blood flow velocity of higher than or equal to 1,300 μm/s and less than 1,500 μm/s in a microcirculatory network capillary is used as a highly-suspected high-velocity blood flow index, and a measured blood flow velocity of higher than or equal to 1,500 μm/s in a microcirculatory network capillary is used as a definite microcirculatory high-velocity blood flow index.

The measurements and calculations of the high-velocity blood flow in the method for measurements and calculations of a microcirculatory high-velocity blood flow should be conducted in an ultra-early stage, an early stage, or a middle stage of sepsis in a body.

In the method for measurements and calculations of a microcirculatory high-velocity blood flow, a blood flow phenomenon that a blood flow velocity in a large capillary network with a diameter of greater than or equal to 20 μm is higher than or equal to 1,500 μm/s is defined as "waterfall blood flow"; and a blood flow phenomenon that a blood flow velocity in a capillary network with a diameter of less than 20 μm is higher than or equal to 1,500 μm/s is defined as "flying mosquitoes blood flow", which are used as the rapid identification image index.

A method for measurements and calculations of a microcirculatory high-velocity blood flow is provided, including: establishing a blood vessel image with a blood flow velocity of higher than 1,000 μm/s as a high-velocity blood flow template or a rapid identification image index; in observation regions of a microcirculation observation device, identifying and selecting, with naked eyes, a blood vessel with a blood flow velocity of higher than 1,000 μm/s as a measurement sample by training or comparing using the high-velocity blood flow template or the rapid identification image index, regardless of the diameter of the blood vessel; tracking a trajectory of a moving RBC, WBC, or plasma particle in the blood vessel; and using a computer to calculate a path length of the RBC, WBC, or plasma particle from a point A to a point B and calculate a time required to travel the path length, and dividing the path length by the time to obtain an average blood flow velocity of the microcirculatory high-velocity blood flow, which solves the problem that the current mainstream measurement method is difficult to accurately measure a high-velocity blood flow velocity of higher than 1,000 μm/s.

The rapid identification image index may include: "waterfall blood flow", which refers to a blood flow phenomenon that a blood flow velocity in a large capillary network with a diameter of greater than or equal to 20 μm is higher than or equal to 1,500 μm/s; and "flying mosquitoes blood flow", which refers to a blood flow phenomenon that a blood flow velocity in a capillary network with a diameter of less than 20 μm is higher than or equal to 1,500 μm/s.

Beneficial effects and principles of the present disclosure:

The research of the present disclosure has shown that a microcirculatory high-velocity blood flow in a sepsis patient will cause abnormal oxygen exchange. In addition to the reason indicated in the blood circulation-microcirculation on page 125 of the Physiology, 9th edition (Literature 8) (when a patient is developed with septic or toxic shock, a large number of arteriovenous shunts and thoroughfare channels are open, and thus the patient is in a shock state but still has warm skin, which is called "warm shock". In this case, as a large amount of arteriole blood enters human venules through anastomotic branches and is not subjected to material exchange with tissue cells, tissue hypoxia may be aggravated, resulting in disease deterioration), there is an important reason for the abnormal oxygen exchange that has been ignored. That is, with the method for measurements of high-velocity blood flow velocity of the present disclosure, it is found that, in sepsis and septic shock, a blood flow velocity in an arteriole, a venule, and a true capillary exchange network (hereinafter referred to as network capillaries) of a microcirculatory capillary circuitous channel is higher than 1,000 μm/s.

It is believed that the phenomenon of a microcirculatory blood flow velocity exceeding a normal limit value for human beings (>1,000 μm/s, as shown on pages 64 to 65 of literature [1]) will still cause oxygen exchange and nutrient exchange disorders. According to the Bernoulli principle of fluid mechanics, in a liquid flow or air flow, a small velocity corresponds to a high pressure and a large velocity corresponds to a low pressure. Although the full conditions of the Bernoulli equation are not satisfied (steady flow, incompressible flow, frictionless flow, and flow along a streamline) in the blood flow with a velocity exceeding a normal limit value, similar conditions can be known. That is, when a flow velocity increases, a pressure of blood on a blood vessel wall decreases, such that oxygen and nutrients will not easily diffuse from a capillary exchange network to cells outside blood vessels to provide oxygen and nutrients for the cells, thereby resulting in oxygen exchange disorder.

Normally, a blood flow in a capillary exchange network of a circuitous channel is very slow, with an average blood flow velocity of 500 μm/s. In fact, the blood flow velocity is merely of 200 μm/s to 300 μm/s in many cases. In this slow flow environment, a pressure inside a capillary is similar to a pressure outside the capillary. Therefore, carbon dioxide and waste thereof in the body can enter the capillary and can be taken away by venous blood, and similarly, oxygen and nutrients in arterial blood can also diffuse out of a blood vessel wall to be absorbed by cells. According to the content on page 65 of Literature [1], a normal microcirculatory blood flow velocity is 0.5 mm/s to 1.0 mm/s. In the above case, a blood flow velocity in a capillary network is increased to more than double the normal limit value, and such a high blood flow velocity will inevitably cause a pressure imbalance on the inner and outer walls of the capillary, thereby leading to partial abnormal oxygen exchange. When pressure on an inner wall of a blood vessel with accelerated blood flow is reduced, oxygen and nutrients will not easily diffuse out from the inner wall of the capillary, and of course, a portion of oxygen and nutrients can diffuse out during this process. Therefore, it is a chronic suffocation process, which is clinically manifested as "warm shock".

The animal experiments of the present disclosure have proved that this oxygen exchange disorder is manifested as the high output-low resistance phenomenon in macro-hemodynamics, namely, "warm shock". In this way, a pathogenic mechanism of sepsis and septic shock has actually been discovered.

The pathogenic mechanism and rescue treatment of sepsis has always been an international problem. At present, the pathogenic mechanism of sepsis is still unclear internationally, as described in the sepsis 3.0 international consensus published in JAMA on Feb. 23, 2016: "There are challenges in defining sepsis and septic shock. Sepsis is a broad term to describe a process that has not been fully known. So far, there has been no simple and clear clinical criteria or biological, imaging, or laboratory characteristics that can uniquely identify a sepsis patient".

In summary, through scientific research, it has been discovered that a microcirculatory high-velocity blood flow causes septic "warm shock", namely, oxygen exchange disorder, and thus the pathogenic mechanism of sepsis can be further revealed. The patent indexes of the present disclosure are established based on the scientific discovery of the sepsis pathogenic mechanism.

In addition, the STD (namely, space-time) is commonly recognized as an algorithm for measuring a high-velocity blood flow internationally. According to the second international consensus of the European Society of Intensive Care Medicine (ESICM) in 2018 (literature 7), the European and American academic consensus in the art insists that: STD is a gold standard for the quantitative detection of RBC flow velocity.

The findings of the present disclosure indicate that a computer can automatically identify the trajectory, shape, and gray level of moving RBC particles, WBC particles, and plasma particles in the microcirculation with a low-velocity blood flow velocity of about 500 μm/s (in which case, the trajectory, shape, and gray level of moving RBC particles, WBC particles, and plasma particles do not change significantly). However, in a high-velocity blood flow, the trajectory, shape, and gray level of moving RBC particles, WBC particles, and plasma particles change significantly, such that the trajectory of the moving RBC particles, WBC particles, and plasma particles cannot be accurately tracked by the space-time method in most cases, which leads to a failed projection of a two-dimensional plane (thus, a length of an adjacent side cannot be calculated by a trigonometric function). Therefore, the space-time method is difficult to successfully measure a velocity of a high-velocity blood flow, and thus cannot be widely used in the measurement of a microcirculatory blood flow velocity of higher than 1,000 μm/s, which is regarded as correcting a common misconception in the industry.

In a first aspect of the present disclosure, the above-mentioned problem is first solved, namely, the problem that the current mainstream measurement method is difficult to accurately measure a high-velocity blood flow velocity of higher than 1,000 μm/s.

In another aspect of the present disclosure, scientific discoveries cannot be patented, but test indexes produced from scientific discoveries and a test method thereof can be patented. In the present patent, a high-velocity blood flow threshold index system and a method for accurately and rapidly measuring a high-velocity blood flow velocity are provided, which can accurately determine the occurrence and development of sepsis. The present invention is used for the early detection of sepsis, the scientific staging of sepsis to adopt different treatment methods, the distinguishing of sepsis from non-infectious systemic inflammatory response syndrome (SIRS), and the resuscitation guidance for sepsis.

According to the scientific research on the pathogenic mechanism of sepsis in the present disclosure, high-velocity blood flow is an important specific imaging index in the early stage of sepsis, and the index can bring the following clinical benefits in the future:

(A) Based on the measurement of high-velocity blood flow, sepsis and septic shock can be discovered at an ultra-early or early stage, and thus more lives of sepsis patients can be saved in time, such as to realize the international "Barcelona Declaration" on Oct. 2, 2002: strive to reduce a sepsis mortality by 25% within 5 years.

(B) With the measurement of high-velocity blood flow as a benchmark, sepsis at different stages can be identified and staged. Clinically, according to the occurrence, development, weakening, and disappearance of high-velocity blood flow, it can be determined that sepsis is in an early, middle or late stage to take proper treatment measures.

(C) Based on the measurement of high-velocity blood flow, septic infection can be effectively distinguished from non-infectious SIRS, which is also a difficult problem in clinical practice at present. Because there is no reliable diagnostic index, misdiagnosis often occurs, that is, general inflammation is easily confused with septic infection, thus delaying the treatment time.

(D) The measurement of high-velocity blood flow can guide a resuscitation process for sepsis. For example, if the high-velocity blood flow gradually weakens, and there is no stagnant blood flow, but a large amount of continuous normal blood flow, it indicates that a resuscitation measure is effective. On the contrary, if the high-velocity blood flow gradually disappears, and there is a large amount of stagnant blood flow, it indicates that a resuscitation measure is ineffective.

The clinical values of the above (A), (B), (C), and (D) have not been recognized in the medical communities of critical care internationally, and the high-velocity blood flow index will not be used to achieve the above (A), (B), (C), and (D) clinical applications in the medical communities of critical care internationally. Therefore, the measurement method and threshold definition for high-velocity blood flow can only be a measurement method and index for microcirculatory blood flow velocity, and cannot be directly used as a disease diagnosis method.

BRIEF DESCRIPTION OF THE DRAWINGS

The present disclosure is further described below based on the accompanying drawings and examples.

FIGURE is an operation interface diagram of the method for measurements and calculations of a microcirculatory high-velocity blood flow according to the present disclosure.

DETAILED DESCRIPTION OF THE EMBODIMENTS

The technical solutions in the examples of the present disclosure are clearly and completely described below in conjunction with the accompanying drawings of the specification. Apparently, the described examples are merely some rather than all of the examples of the present disclosure. The following description of at least one exemplary example is merely illustrative, and not intended to limit the present disclosure and application or use thereof in any way. All other examples obtained by a person of ordinary skill in the art based on the examples of the present disclosure without creative efforts shall fall within the protection scope of the present disclosure.

The technologies, methods, and equipment known to those skilled in the art may not be discussed in detail, but where appropriate, the technologies, methods, and equipment should be regarded as part of the authorized specification. A system for measurements and calculations of a microcirculatory high-velocity blood flow is provided, including:

a data acquisition module configured to select and acquire microcirculatory blood vessel image data;

a storage module configured to store the acquired microcirculatory blood vessel image data;

a velocity measurement module configured to measure a traveling distance and a traveling time of RBC, WBC, or plasma particles in a blood vessel sample and calculate a ratio of the traveling distance to the traveling time to obtain a blood flow velocity; and a high-velocity blood flow index module configured to determine an index level for the microcirculatory high-velocity blood flow, where the microcirculatory high-velocity blood flow is defined as a microcirculation manifestation of a macro-hemodynamic high output-low resistance phenomenon in a resting state; and specifically, a blood flow velocity of higher than 1,000 μm/s in an arteriole, a venule, and a true capillary exchange network of a microcirculatory capillary circuitous channel is set as an initial threshold for the high-velocity blood flow.

The high-velocity blood flow index module may include the following three parameter indexes:

a first level: a blood flow velocity of higher than or equal to 1,000 μm/s and less than 1,300 μm/s in a microcirculatory network capillary, indicating that it is suspected of high-velocity blood flow;

a second level: a blood flow velocity of higher than or equal to 1,300 μm/s and less than 1,500 μm/s in a microcirculatory network capillary, indicating that it is highly suspected of high-velocity blood flow; and a third level: a blood flow velocity of higher than or equal to 1,500 μm/s in a microcirculatory network capillary, indicating that there is definitely a microcirculatory high-velocity blood flow.

The system for measurements and calculations of a microcirculatory high-velocity blood flow may further include a high-velocity blood flow template or rapid identification image index module; the high-velocity blood flow template or rapid identification image index module may store a blood vessel image with a blood flow velocity of higher than 1,000 μm/s as a high-velocity blood flow template or a rapid identification image index; and the rapid identification image index may include: "waterfall blood flow", which refers to a blood flow phenomenon that a blood flow velocity in a large capillary network with a diameter of greater than or equal to 20 μm is higher than or equal to 1,500 μm/s; and "flying mosquitoes blood flow", which refers to a blood flow phenomenon that a blood flow velocity in a capillary network with a diameter of less than 20 μm is higher than or equal to 1,500 μm/s.

A method for measurements and calculations of a microcirculatory high-velocity blood flow is provided, including the following steps:

step 1: defining the microcirculatory high-velocity blood flow as a microcirculation manifestation of a macro-hemodynamic high output-low resistance phenomenon in a resting state, where specifically, a blood flow velocity of higher than 1,000 μm/s in an arteriole, a venule, and a true capillary exchange network of a microcirculatory capillary circuitous channel is set as an initial threshold for the high-velocity blood flow;

step 2: using a microcirculation observation device to select 3 to 5 observation regions at sublingual mucosa or other parts of a body that allow microcirculation observation and record videos of the observation regions; comparing the videos of the 3 to 5 observation regions, selecting a video with the highest blood flow velocity as a high-velocity blood flow candidate sample A1 from videos each with a blood vessel having a blood flow velocity of higher than 1,000 μm/s, and storing the high-velocity blood flow candidate sample A1 in a sample database; and selecting a blood vessel B1 with the highest blood flow velocity in the candidate sample A1 as a high-velocity blood flow candidate blood vessel sample A1-B1, regardless of the diameter of the blood vessel, which is the most fundamental principle of the method; and step 3: tracking a trajectory of RBC, WBC, or plasma particles in the high-velocity blood flow on a display screen, calculating a traveling distance and a corresponding traveling time of the tracked RBC, WBC, or plasma particles with the aid of a computer, and dividing the traveling distance by the traveling time to calculate an average blood flow velocity of the high-velocity blood flow, which solves the problem that the current mainstream measurement method is difficult to accurately measure a high-velocity blood flow velocity of higher than 1,000 μm/s.

The method for measurements and calculations of a microcirculatory high-velocity blood flow may further include step 4: evaluating the microcirculatory high-velocity blood flow; and because a current technical means fails to measure a velocity of a high-velocity blood flow very accurately, a measured blood flow velocity of higher than or equal to 1,000 μm/s and less than 1,300 μm/s in a microcirculatory network capillary is used as a suspected high-velocity blood flow index, a measured blood flow velocity of higher than or equal to 1,300 μm/s and less than 1,500 μm/s in a microcirculatory network capillary is used as a highly-suspected high-velocity blood flow index, and a measured blood flow velocity of higher than or equal to 1,500 μm/s in a microcirculatory network capillary is used as a definite microcirculatory high-velocity blood flow index.

The measurements and calculations of the high-velocity blood flow in the method for measurements and calculations of a microcirculatory high-velocity blood flow should be conducted in an ultra-early stage, an early stage, or a middle stage of sepsis in a body.

In the method for measurements and calculations of a microcirculatory high-velocity blood flow, a blood flow phenomenon that a blood flow velocity in a large capillary network with a diameter of greater than or equal to 20 μm is higher than or equal to 1,500 μm/s is defined as "waterfall blood flow"; and a blood flow phenomenon that a blood flow velocity in a capillary network with a diameter of less than 20 μm is higher than or equal to 1,500 μm/s is defined as "flying mosquitoes blood flow", which are used as the rapid identification image index.

As shown in FIGURE, a method for measurements and calculations of a microcirculatory high-velocity blood flow is provided, including: establishing a blood vessel image with a blood flow velocity of higher than 1,000 μm/s as a high-velocity blood flow template or a rapid identification image index; in observation regions of a microcirculation observation device, identifying and selecting, with naked eyes, a blood vessel with a blood flow velocity of higher than 1,000 μm/s as a measurement sample by training or comparing using the high-velocity blood flow template or the rapid identification image index, regardless of the diameter of the blood vessel; tracking a trajectory of a moving RBC, WBC, or plasma particle in the blood vessel; and using a computer to calculate a path length of the RBC, WBC, or plasma particle from a point A to a point B and calculate a time required to travel the path length, and dividing the path length by the time to obtain an average blood flow velocity of the microcirculatory high-velocity blood flow, which solves the problem that the current mainstream measurement method is difficult to accurately measure a high-velocity blood flow velocity of higher than 1,000 μm/s. As shown in FIGURE, the high-velocity blood flow in a capillary with a diameter of 6.57 μm has a velocity of 1,529.54 μm/s. In clinical videos of high-velocity blood flow in sublingual microcirculation of sepsis patients like FIGURE, the highest blood flow velocity measured is 3,200 μm/s, and some septic shock patients have a low blood flow velocity of about 1,500 μm/s.

The rapid identification image index may include: "waterfall blood flow", which refers to a blood flow phenomenon that a blood flow velocity in a large capillary network with a diameter of greater than or equal to 20 μm is higher than or equal to 1,500 μm/s; and "flying mosquitoes blood flow", which refers to a blood flow phenomenon that a blood flow velocity in a capillary network with a diameter of less than 20 μm is higher than or equal to 1,500 μm/s.

A principle of the present disclosure to accurately discover and measure a microcirculatory high-velocity blood flow is as follows:

(1) The microcirculatory high-velocity blood flow is defined as a microcirculation manifestation of a macro-hemodynamic high output-low resistance phenomenon in a resting state, and specifically, a blood flow velocity of higher than 1,000 μm/s in an arteriole, a venule, and a true capillary exchange network (hereinafter referred to as network capillaries) of a microcirculatory capillary circuitous channel is set as an initial threshold for the high-velocity blood flow.

(2) Further, a microcirculation observation device is used to select 3 to 5 observation regions at sublingual mucosa or other parts of a body that allow microcirculation observation and record videos of the observation regions; the videos of the 3 to 5 observation regions are compared, and a video with the highest blood flow velocity is selected as a high-velocity blood flow candidate sample A1 from videos each with a blood vessel having a blood flow velocity of higher than 1,000 μm/s, and stored in a sample database; and a blood vessel B1 with the highest blood flow velocity in the candidate sample A1 is selected as a high-velocity blood flow candidate blood vessel sample A1-B1, regardless of the diameter of the blood vessel, which is the most fundamental principle of the method.

(3) Further, the STD (namely, space-time) is commonly recognized as an algorithm for measuring a high-velocity blood flow at present. However, in a high-velocity blood flow, the trajectory, shape, and gray level of moving RBC, WBC, and plasma particles in a blood vessel change significantly, such that this method cannot be widely used to accurately measure a microcirculatory blood flow velocity of higher than 1,000 μm/s, which corrects a common misconception in the industry, indicating a dead end. Therefore, in order to meet the urgent demand for reliable high-velocity blood flow measurement in clinical acute and severe cases, a trajectory of RBC, WBC, or plasma particles in a high-velocity blood flow is tracked with naked eyes, a traveling distance and a corresponding traveling time of the RBC, WBC, or plasma particles are calculated with the aid of a computer, and the traveling distance is divided by the traveling time to calculate an average blood flow velocity of the high-velocity blood flow. This method is also a revolution for the space-time method among the current mainstream technologies for measuring a microcirculatory blood flow velocity.

Although it is commonly known that a value obtained by dividing a distance by a time is a velocity value, in the case where the space-time method is generally recognized as a gold standard for measuring a blood flow velocity in the art, it is proposed that the space-time method is generally invalid for the measurement of a high-velocity blood flow velocity, and thus the method of tracking RBC, WBC, or plasma particles with naked eyes instead and calculating a traveling distance and a corresponding traveling time of the RBC, WBC, or plasma particles with a computer is provided to solve the problem that the current mainstream measurement method cannot be widely used to accurately measure a high-velocity blood flow velocity of higher than 1,000 μm/s, which is an innovation and also corrects the misconception in the art that the space-time method is generally recognized as a gold standard for measuring a high-velocity blood flow velocity.

(4) Further, because a current technical means fails to measure a velocity of a high-velocity blood flow very accurately, a measured blood flow velocity of about 1,000 μm/s to 1,300 μm/s in a microcirculatory network capillary is used as a suspected high-velocity blood flow index, a measured blood flow velocity of about 1,300 μm/s to 1,500 μm/s in a microcirculatory network capillary is used as a highly-suspected high-velocity blood flow index, and a measured blood flow velocity of higher than 1,500 μm/s in a microcirculatory network capillary is used as a definite microcirculatory high-velocity blood flow index.

(5) Further, the measurements and calculations of the high-velocity blood flow should be conducted in an ultra-early stage, an early stage, or a middle stage of sepsis. The measurements and calculations of the high-velocity blood flow will fail if conducted in the advanced stage of sepsis when the high-velocity blood flow has gradually disappeared. European and American scholars stated in a published article (literature 4) that no high-velocity blood flow was found. This is because the European and American scholars did not know that a high-velocity blood flow has different development stages, and mistakenly tried to measure and find a high-velocity blood flow in some patients with sepsis at advanced stage, which would definitely fail. This is also a long-term misconception, and thus no progress has been made in the study of sepsis in European and American academic circles.

(6) Further, in sublingual microcirculation of patients with sepsis and septic shock, a high-velocity blood flow is observed in a large capillary network (with a diameter of greater than or equal to 20 μm), which is very similar to a "waterfall" flow due to a high flow velocity and thus is called "waterfall blood flow" to facilitate identification; and a high-velocity blood flow also appears in a capillary network with a diameter of less than 20 μm, which is not like a waterfall, but like a swarm of mosquitos in summer, and thus is called "flying mosquitoes blood flow". The vivid naming of these two high-velocity blood flow phenomena will bring benefits to the identification of high-velocity blood flow in the future, because these two names are very vivid and easy to understand and remember.

Application Example 1: (these Examples are Only a Part of the Present Disclosure)

In the QSOFA test and evaluation of sepsis, the sublingual microcirculatory high-velocity blood flow test was conducted for suspected sepsis patients, that is, the patients with/without fever who had a systolic pressure of less than or equal to 100 mmHg, a respiratory rate of greater than or equal to 22/min, or altered consciousness. This test is simple, efficient, and non-invasive, and thus can be conducted in an emergency room. In the test, a blood vessel with the highest blood flow velocity was selected from blood vessels with a blood flow velocity of higher than 1,000 μm/s, and a blood flow velocity of the blood vessel was measured. Because a current technical means fails to measure a velocity of a high-velocity blood flow very accurately, a measured blood flow velocity of about 1,000 μm/s to 1,300 μm/s in a sublingual microcirculatory network capillary was used as a suspected high-velocity blood flow index, a measured blood flow velocity of about 1,300 μm/s to 1,500 μm/s in a sublingual microcirculatory network capillary was used as a highly-suspected high-velocity blood flow index, and a measured blood flow velocity of higher than 1,500 μm/s in a sublingual microcirculatory network capillary was used as a definite microcirculatory high-velocity blood flow index.

If a suspected high-velocity blood flow or a high-velocity blood flow is found, it can be tracked in time, and then comprehensive determination and diagnosis can be conducted by combining various traditional indexes, such that a rescue measure can be taken as soon as possible.

Application Example 2: The sublingual microcirculation was routinely monitored for patients with common pneumonia. In most of the patients with common pneumonia, no blood vessel with a blood flow velocity of higher than 1,000 μm/s was found in the sublingual microcirculation, but a blood flow velocity of 2,300 μm/s was found in one patient. The patient was immediately tracked and continuously observed, and the patient showed warm shock symptoms, such that a case where common pneumonia was transformed into severe septic pneumonia was discovered in time.

The above are merely exemplary examples of the present disclosure, and are not intended to limit the present disclosure. Any modifications, equivalent replacements, improvements, and the like made within the spirit and principle of the present disclosure shall be all included in the protection scope of the present disclosure.

What is claimed is:

1. A method for measurements and calculations of a microcirculatory high-velocity blood flow, comprising the following steps:
   step 1: defining the microcirculatory high-velocity blood flow as a microcirculation manifestation of a macrohemodynamic high output-low resistance phenomenon in a resting state, and setting a blood flow velocity of higher than 1,000 μm/s in an arteriole, a venule, and a true capillary exchange network of a microcirculatory capillary circuitous channel as an initial threshold for the microcirculatory high-velocity blood flow;

step 2: using a microcirculation observation device to select 3 to 5 observation regions at a sublingual mucosa or any other part of a body that allows microcirculation observation and recording videos of the 3 to 5 observation regions; comparing the videos of the 3 to 5 observation regions, selecting a video with a highest blood flow velocity from the videos with blood vessels with blood flow velocity higher than 1,000 μm/s as a high-velocity blood flow candidate sample, and saving the high-velocity blood flow candidate sample in a sample database; and then in the high-velocity blood flow candidate sample selecting a blood vessel with a highest blood flow velocity as a candidate blood vessel sample of the high-velocity blood flow candidate blood vessel sample, without considering a diameter of the blood vessel; and step 3: tracking a trajectory of RBCs, WBCs, or plasma particles in the microcirculatory high-velocity blood flow on a display screen, calculating a traveling distance and a traveling time of the RBCs, the WBCs, or the plasma particles with an aid of a computer, and dividing the traveling distance by the traveling time to calculate an average blood flow velocity of the microcirculatory high-velocity blood flow.

2. The method according to claim 1, further comprising step 4: evaluating the microcirculatory high-velocity blood flow, wherein a measured blood flow velocity of higher than or equal to 1,000 μm/s and less than 1,300 μm/s in a microcirculatory network capillary is used as a suspected high-velocity blood flow index, a measured blood flow velocity of higher than or equal to 1,300 μm/s and less than 1,500 μm/s in the microcirculatory network capillary is used as a highly-suspected high-velocity blood flow index, and a measured blood flow velocity of higher than or equal to 1,500 μm/s in the microcirculatory network capillary is used as a definite microcirculatory high-velocity blood flow index.

3. The method according to claim 1, wherein the measurements and the calculations of the microcirculatory high-velocity blood flow are conducted in an ultra-early stage, an early stage, or a middle stage of sepsis in the body.

4. The method according to claim 1, wherein a blood flow phenomenon that a blood flow velocity is higher than or equal to 1,500 μm/s in a large capillary network with a diameter of greater than or equal to 20 μm is defined as a "waterfall" blood flow; and a blood flow phenomenon that a blood flow velocity is higher than or equal to 1,500 μm/s in a capillary network with a diameter of less than 20 μm is defined as a "flying-mosquitoes" blood flow, wherein the "waterfall" blood flow and the "flying-mosquitoes" blood flow are used as indexes for rapid image identification.

5. A method for measurements and calculations of a microcirculatory high-velocity blood flow, comprising:
establishing a blood vessel image with a blood flow velocity of higher than 1,000 μm/s as a template of the high-velocity blood flow or an image index for rapid identification;

in observation regions of a microcirculation observation device, by training with naked eyes through the comparison with the high-velocity blood flow template or the rapid identification image index, identifying and selecting a blood vessel with a blood flow velocity of higher than 1,000 μm/s as a measurement sample, regardless of a diameter of the blood vessel;

tracking a trajectory of a moving RBC, a moving WBC, or a moving plasma particle in the blood vessel; and using a computer to calculate a path length of the moving RBC, the moving WBC, or the moving plasma particle from a first point to a second point and calculate a time required to travel the path length, and dividing the path length by the time to obtain an average blood flow velocity of the microcirculatory high-velocity blood flow.

6. The method according to claim 5, wherein the rapid identification image index comprises:
a "waterfall" blood flow and a "flying-mosquitoes" blood flow, wherein the "waterfall" blood flow refers to a blood flow phenomenon that a blood flow velocity in a large capillary network with a diameter of greater than or equal to 20 μm is higher than or equal to 1,500 μm/s; and the "flying-mosquitoes" blood flow refers to a blood flow phenomenon that a blood flow velocity in a capillary network with a diameter of less than 20 μm is higher than or equal to 1,500 μm/s.

7. The method according to claim 2, wherein the measurements and the calculations of the microcirculatory high-velocity blood flow are conducted in an ultra-early stage, an early stage, or a middle stage of sepsis in the body.

8. The method according to claim 2, wherein a blood flow phenomenon that a blood flow velocity is higher than or equal to 1,500 μm/s in a large capillary network with a diameter of greater than or equal to 20 μm is defined as a "waterfall" blood flow; and a blood flow phenomenon that a blood flow velocity is higher than or equal to 1,500 μm/s in a capillary network with a diameter of less than 20 μm is defined as a "flying-mosquitoes" blood flow, wherein the "waterfall" blood flow and the "flying-mosquitoes" blood flow are used as a rapid identification image index.

* * * * *